United States Patent
Ferguson

(10) Patent No.: US 6,455,569 B1
(45) Date of Patent: Sep. 24, 2002

(54) CONNECTIVE TISSUE SOFTENING

(75) Inventor: Mark W. J. Ferguson, Derbyshire (GB)

(73) Assignee: Renovo LTD, Manchester (DE)

( * ) Notice: Subject to any disclaimer, the term of this patent is extended or adjusted under 35 U.S.C. 154(b) by 0 days.

(21) Appl. No.: 09/913,713

(22) PCT Filed: Feb. 14, 2000

(86) PCT No.: PCT/GB00/00474

§ 371 (c)(1),
(2), (4) Date: Aug. 17, 2001

(87) PCT Pub. No.: WO00/48617

PCT Pub. Date: Aug. 24, 2000

(30) Foreign Application Priority Data

Feb. 18, 1999 (GB) ................................. 9903598

(51) Int. Cl.$^7$ ....................... A61K 31/535; A61K 31/53; A61K 31/40
(52) U.S. Cl. ...................... 514/419; 514/243; 514/238.2
(58) Field of Search ................. 514/419, 243, 514/238.2

(56) References Cited

U.S. PATENT DOCUMENTS

| 5,240,958 A | 8/1993 | Crimmin et al. |
| 5,310,759 A | 5/1994 | Bockman |

FOREIGN PATENT DOCUMENTS

| DE | 195 42 189 | 5/1997 |
| EP | 0 574 758 | 12/1993 |
| WO | WO95/24921 | 9/1995 |
| WO | WO99/03979 | 1/1999 |

OTHER PUBLICATIONS

Moses et al, "Temporal Study of the Activity of Matrix Metalloproteinases and Their Endogenous Inhibitors During Wound Healing", Journal of Cellular Biochemistry 60:379–386 (1996).

Database Biosis Online! Biosciences Information Service, Philadelphia, PA, US; Dec. 1998, Ganu Vishwas et al: "Inhibition of interleukin–1alpha–induced cartilage oligomeric matrix protein degradation in bovine articular cartilage by matrix metalloproteinase inhibitors." Database accession No. PREV199900079331, XP002151898 abstract & Arthritis & Rheumatism, vol. 41, No. 12, Dec. 1998, pp. 2143–2151.

Database Biosis Online! Biosciences Information Service, Philadelphia, PA, US; Oct. 1998, Kozaci L D et al: "Stromelysin 1, neutrophil collagenase, and collagenase 3 do not play major roles in a model of chondrocyte mediated cartilage breakdown." Database accession No. PREV19990005122, XP002151899 abstract & Molecular Pathology, vol. 51, No. 5, Oct. 1998, pp. 282–286.

Marcotte et al, "Evaluation of the Inhibition of Other Metalloproteinases by Matrix Metalloproteinase Inhibitors", J. Enzyme Inhibition 14:425–435 (1999).

Brown, Peter D., "Clinical studies with matrix metalloproteinase inhibitors", APMIS 107:174–180 (1999).

Yip et al, "Matrix metalloproteinase inhibitors: applications in oncology", Investigational New Drugs 17:387–399 (1999).

Marquoi et al, "Inhibition of matrix metalloproteinase 2 maturation ahd HT1080 invasiveness by a syntheitc furin inhibitor", FEBS Letters 424:262–266 (1998).

Krumme et al, "Hydroxamate derivatives of substrateanalogous peptides containing aminomalonic acid are potent inhibitors of matrix metalloproteinases", FEBS 436:209–212 (1998).

Kahari and Saarialho–Kere, "Matrix metalloproteinases and their inhibitors in tumour growth and invasion", Ann. Med. 31:34–45 (1999).

Brown, Peter D., "Matrix metalloproteinase inhibitors", Breast Cancer Research and Treatment 52:125–136 (1998).

*Primary Examiner*—Zohreh Fay
*Assistant Examiner*—Brian-Yong S. Kwon
(74) *Attorney, Agent, or Firm*—Nixon & Vanderhye P.C.

(57) ABSTRACT

The use of Matrix Metalloproteinase Inhibitors in the prevention or treatment of connective tissue softening and also for the maintenance of sutures in such connective tissues. The connective tissue may be a tendon, ligament or cartilage.

11 Claims, No Drawings

CONNECTIVE TISSUE SOFTENING

This application is a 371 of International Application No. PCT/GB00/00474, filed Feb. 14, 2000, which claims priority from GB Application No. 9903598.2 filed Feb. 18, 1999.

The present invention relates to the prevention or treatment of connective tissue softening.

Injury to connective tissues such as tendons, ligaments and cartilage may occur in a number of ways. For instance, a tendon may be ruptured or torn following a sudden twist or pull on a joint to which the tendon is fixed. Connective tissue injuries may also arise due to a gross trauma such as a crush injury or an incisional wounding of a tissue. Alternatively connective tissue injuries may arise as a result of repetitive trauma to a tissue (e.g. repetitive strain injuries caused by prolonged use of pneumatic drills).

Connective tissue injuries of the limbs (e.g. tendon injuries of the fingers, wrist or legs) of humans and animals are particularly problematic.

To repair connective tissue it is necessary for the areas of tissue (e.g. the torn edges of a severed tendon) to be maintained in close proximity following which reparative processes generate a tissue which bridges the gap between undamaged tissues. The areas may be brought into close proximity by immobilising the tissues or by surgical intervention (e.g. by suturing the torn edges together).

However, during the first few days following an injury (usually up to 7 days but possibly up to 14 days) a phenomenon known as "softening" occurs which can have deleterious effects on tissue repair. Softening involves the liquefaction of the extracellular matrix at the edges of damaged connective tissue.

This liquefaction represents a problem for several reasons. In the first place the softened tissue is very weak and may easily be torn leading to re-injury and even permanent disability. This is particularly problematic for load bearing connective tissues such as injured tendons in the leg. Furthermore, the weakening caused by softening can be such that the tensile strength of the connective tissue actually becomes less than it was immediately after the injury occurred. For example, 5 days after a finger tendon is sutured together the tendon often only has 10–20% of the tensile strength that it had immediately post operatively and only about 1% of the tensile strength of a uninjured tendon.

Furthermore, if surgery is used, softening is also a problem because the softened tissues may be difficult to maintain in close proximity to each other due to the fact that sutures often come out of the liquefied tissues and the torn ends may then separate preventing any repair from occurring.

In the case of repetitive strain injuries (which involve frequent "re-injury") connective tissues such as tendons and ligaments may be in a chronic "softened" state. When this is the case the tissue often has an outer sheaf of apparently normal connective tissue but comprises an inner core of liquefied tissues. Any injury to the outer sheaf may rupture the tissue with serious consequences for connective tissue function.

Connective tissue softening is highly problematic during connective tissue healing in people and animals (particularly horses and pets) and there is a need to provide medicaments that prevent connective tissue softening from occurring.

According to a first aspect of the present invention there is provided the use of a Matrix Metalloproteinase Inhibitor in the manufacture of a medicament for use in the treatment or prevention of connective tissue softening.

According to a second aspect of the present invention there is provided a method of preventing or treating connective tissue softening comprising administering to a subject in need of treatment a therapeutically effective amount of a Matrix Metalloproteinase Inhibitor.

The inventors have found that matrix metalloproteinase (MMP) inhibitors are effective for inhibiting or preventing connective tissue softening. These inhibitors may therefore be used to promote the healing of injuries to connective tissues such as tendons, ligaments and cartilage in people and animals. For example, a person with a torn tendon of the finger benefits from the administration of MMP inhibitors because the subsequent reduction in softening results in the edges of the torn tendon knitting together more quickly and with greater strength than seen for untreated tendons. MMP inhibitors are also highly suitable for administration to animals (such as dogs or horses and particularly valuable race or show animals) for the treatment or prevention of connective tissue softening and especially tendon injuries of the legs. By treating a horse with an MMP inhibitor according to the present invention it is possible to prevent, or significantly decrease the chances of, the animal becoming lame following a connective tissue injury (e.g. of a tendon). Thus the use of MMP inhibitors according to the present invention makes it less likely that such an expensive animal would need to be put down following an injury.

MMP inhibitors are particularly useful for maintaining sutures in a connective tissue (e.g. a healing tendon) and according to a third aspect of the present invention there is provided the use of a Matrix Metalloproteinase Inhibitor in the manufacture of a medicament for maintaining sutures in a connective tissue.

According to a fourth aspect of the present invention there is provided a method for maintaining sutures in a connective tissue comprising administering to a subject in need of treatment a therapeutically effective amount of a Matrix Metalloproteinase Inhibitor.

We have found that MMP inhibitors reduce tissue softening and thereby help to maintain sutures in a required position. It is preferred that MMP inhibitors are used according to the third or fourth aspects of the invention to maintain sutures in a healing tendon. This allows for improved healing of the ends of a severed tendon because the sutures are more able to maintain the severed ends of the tendon in close proximity.

Matrix metalloproteinases (MMPs) are a family of $Zn^{-+}$ dependent neutral metalloendopeptidases. Phylogenetically they are from the Matrixin subfamily of Family M10 of the MB clan of Metallopeptidases that have HEXGHXXGXXHS Zinc-Binding Motifs. Two conserved histidine residues and a glutamate immobilise the zinc ion at the active site. At least eleven different types of MMP are known and are designated MMP 1–13, MT-1 MMP and also PUMP 1.

MMPs are secreted in an inactive zymogen form following, cleavage of a signal peptide. They then require further proteolytic cleavage to become activated in the extracellular environment. The activation of MMPs can occur via many mechanisms, these include chaotropic agents (e.g. sodium dodecyl sulphate), low pH, chemicals which can oxidise the sulphydryl group (e.g. N-methyl maleimide) or enzyme proteolysis. In vivo it is likely that the first step of activation is mediated by serine proteinases such as trypsin, plasmin, cathepsin G and kallikrein or other MMPs. These proteases remove part of a 10 kDa propeptide on the N-amino side of a cysteine residue which, in the inactive form is covalently linked by a sulphydryl bond to the zinc atom at the centre of the active region. This bond is consequently destabilised and the remainder of the propeptide region is auto catalytically cleaved, producing the active enzyme.

In vitro substrate specificity varies between the different types of MMP although all MMP are able to degrade at least one extra cellular matrix component (e.g. collagen). Different MMs can lyse the same substrate, although different affinities and kinetics are apparent between the MMPs for a particular substrate. Each MMP can also lyse a variety of substrates although some substrate preference is apparent (see Table 1). Binding of MMP to substrate is site specific, the MMP binding to a particular part of the substrate molecule, and involves the N or the C terminal of the enzyme, which is a specific MMP dependent event. With the exception of MMP-8 and MMP-9 in Neutrophils, MMPs are not found sequestered in storage granules in cells. They are synthesised in response to cell signals and MMP production is controlled at the transcriptional level.

TABLE 1

Matrix Metalloproteinases and In vitro Substrate Specificity

| ENZYMES | MMP NO./ EC. NO. | MW DA PROENZYME/ ACTIVE | SUBSTRATE |
|---|---|---|---|
| 1. Interstitial Collagenase Group | | | |
| Fibroblast Type | MMP-1 3.4.24.7 | 52000/42000 | I, II, III, VII, VIII, X Collagens, Gelatin, IGFBP-3 |
| Neutrophil Type | MMP-8 3.4.24.34 | 58000/57000 | I, II, III Collagens |
| Collagenase-III | MMP-13 | 65000/55000 48000 | I, II, III Collagens, Gelatin |
| 2. Gelatinase/Type IV Collagenase Group | | | |
| Gelatinase A | MMP-2 3.4.24.24 | 72000/67000 | I, IV, V, VII, X Collagens, Gelatin, Fibronectin, Elastin |
| Gelatinase B | MMP-9 3.4.24.35 | 92000/67000 | IV, V, VII, X Collagens, Gelatin, Elastin |
| 3. Stromelysin Group | | | |
| Stromelysin-1 | MMP-3 3.4.24.17 | 57000/45000 28000 | Proteoglycan, MMPs-1–9, Fibronectin, IV, V, VII, IX, X Collagens, Laminin, Gelatin as for MMP-3 |
| Stromelysin-2 | MMP-10 3.4.24.22 | 57000/48000 28000 | |
| Stromelysin-3 | MMP-11 | 58000/28000 | Proteoglycan/ Fibronectin, Gelatin, Laminin, Collagen IV |
| 4. Others | | | |
| Matrilysin (PUMP-1) | MMP-7 3.4.24.23 | 28000/19000 | Gelatin, Elastin, Fibronectin, Laminin, Proteoglycans, Collagen IV, MMPs1–9 |
| Macrophage Metalloelastase | MMP-12 | 54000/45000 22000 | Elastin, Fibronectin |
| Membrane Type MMP | MT-MMP | 66000/ | MMP-2 |

The activity of MMPs may be modulated in a variety of ways. In vivo activity is tightly regulated both at the transcriptional level and in the extra-cellular space.

Transcriptional regulation is sensitive to many growth factors, including; IL-1α, IL-4, IL-6, IL-10, platelet derived growth factor (PDGF), basic fibroblast growth factor (FGF-2), TGF-α, and TGF-β. Most of the regulatory pathways converge on the AP-1 promoter region of the MMP genes (except that of MMP-2 Which is normally constitutively expressed). Other promoter sequences include PEA3 and TRE. Pathway convergence is at the level of c-fos and c-jun translation.

Jun and Fos proteins form heterodimers which bind to AP-1 in the promoter region of MMPs and thereby up-regulate transcription. Dexamethasone and other steroid hormones disrupt this pathway by binding to Jun protein. Prostaglandins up-regulate regulate MMP synthesis whereas retinoic acids, via cjun, down-regulate MMP synthesis. Binding of fibroblasts to various tenascin/fibronectin ligands, via an integrin dependent mechanism, which shows a loss of Focal Adhesion Kinase (FAK) also regulates MMP-1 expression through Fos/AP-1 activation. It is therefore of great interest that alterations of cell morphology leading to perturbations of the cytoskeleton (CSK), have been demonstrated to trigger expression of TGF-$β_1$, and MMP-1, suggesting that events in vivo may be mediated by cell morphology and integrin signalling as TGF-$β_1$ down-regulates MMP-1 production. Cellular exposure to signalling stimuli has divergent effects on synthesis of individual MMPs, with MMP-1 and 3 being down-regulated by TGF-β which conversely up-regulates MMP-2

MMP activity is tightly controlled in the extra-cellular space and extra-cellular matrix (ECM). Activation of latent zymogens is controlled by inhibitors of serine proteases. An example of this is plasminogen activator inhibitor-i (PAI1). Expression influences the activation of MMPs indirectly via inhibition of plasminogen activation and therefore inhibition of plasmin activation.

The proteolytic action of MMPs requires the presence of $Ca^{++}$ for active tertiary conformation and as a consequence, the calcium ion chelator EDTA inactivates MMPs.

An important form of regulation of MMPs in the ECM is through the activity of specific inhibitors of MMPs known as Tissue inhibitors of metalloproteinases (TIMPs). At least three types of vertebrate TIMP are known (TIMP-1, 2 and 3). These are part of a family of 8 TIMPs defined by a highly conserved secondary structure involving six disulphide bonds. TIMPs bind to MMPs with a 1:1 stoichiometry and inactivate the enzyme. They are frequently produced by the same cell producing MMPs and as the TIMP-MMP binding is tight, production of equimolar concentrations would not lead to an effect on ECM degradation. Thus subtle perturbations in extra-cellular concentrations of either could have a significant impact on ECM degradation.

TIMP-1 is inducible, glycosylated and X-linked whereas TIMP-2 appears to be constitutively expressed, non-glycosylated and autosomal. TIMP-1 like many of the MMPs has an AP-1 promoter region upstream. This may explain the co-ordinate expression of MMPs and TIMP-1. TGF-β, retinoic acid and female sex hormones, however, up-regulate TIMP-1 and down-regulate the expression of some MMPs. TGF-β specifically up-regulates MMP-2 and 9 and TIMP-1 down-regulates MMP-1 and 3. This contrasts with the actions of IL-4 which down-regulates both MMP-1 and 2 and has no effect on TIMP, which further contrasts with FGF-2 which has an effect through up-regulating MMP-1 and TIMP-1. This would enable complex cocktails of growth factors to have very subtle influences on tissue degradation.

All TIMPs bind all active MMPs and inhibit them although with varying affinities. Both the N and C terminal domains appear to be important in TIMPs for binding, although the binding of TIMPs to active MMPs seems to involve a variety of mechanisms. TIMP-2 binds pro-MMP-2 and TIMP-1 binds pro-MMP-9. Both these enzymes are capable of subsequent activation, albeit at a lower level and the presence of TIMPs appear to stabilise them against subsequent loss of activity through further cleavage. TIMP-3, like TIMPs 1 and 2, has growth factor like properties, extensive intra-chain disulphide bonding, a molecular weight of 24 kDa and is synthesised in fibroblasts. TIMPs concentration in the ECM is probably regulated through their susceptibility to proteolysis by serine proteases. This mechanism may control local concentration in the ECM.

MMPs are also inactivated by $\beta_2$-macroglobulin. This appears to be a mechanism for regulating MMP activity both in the ECM and in plasma. Regulation of catalytic cleavage of active MMPs through autocatalysis or through catalysis by other ECM proteinases may also control MMP activity in the ECM.

While we do not wish to be bound by any hypothesis, we believe that connective tissue softening is brought about by an up-regulation in the expression of MMPs in connective tissue cells and from inflammatory cells at the injured site. We believe this up-regulation leads to digestion of components of the extracellular matrix and subsequent liquifaction (i.e. softening). MMP inhibitors are effective for preventing softening by counteracting this increase in MMP activity The term "MMP inhibitor" is used herein to mean agents or compounds which will reduce, limit or prevent MMP from having its physiological effect (i.e. the inhibitor will reduce, limit or prevent the enzymic digestion of extracellular matrix molecules by MMP). By "MMP inhibitor" we also mean agents or compounds which prevent or reduce the production or secretion of MMP, degrade MMP or sequester MMP or any negative regulator of MMP activity described in the preceding paragraphs.

Preferred MMP inhibitors prevent MMP production by a cell. For example, agents may prevent MMP gene transcription, prevent translation of MMP from MMP mRNA, disrupt post-translational modification of MMP, disrupt MMP secretion from the cell in which it is expressed or prevent the formation of active MMP from the zymogen. Alternatively, the inhibitor may be an agent which increases degradation of MMP, such as a proteolytic enzyme. Equally the inhibitor may be an agent which prevents MMP combining with its substrate such as a neutralising antibody against MMP or an aptamer against MMP. The inhibitor may also be an antisense oligonucleotide or ribozyme against MMP mRNA or the MMP gene as appropriate.

Most preferred MMP inhibitors are compounds which selectively inhibit the enzymic action of MMPs by binding to MMP. These may be competitive inhibitors (i.e. those which compete for the active site of MMP) or non-competitive inhibitors (such as allosteric inhibitors or compounds which covalently modify the active site of MMP).

Both natural and synthetic MMP inhibitors are known and may be used according to the present invention. Examples of such naturally occurring MMP inhibitors are $\alpha_2$-macroglobulin (a collagenase inhibitor found in blood) and Tissue Inhibitors of MMPs (TIMPS—see above).

Preferred synthetic MMP inhibitors include GM6001 (Trade name Galardin) and Batimastat (BB-94). Most preferred synthetic MMP inhibitors are ganic molecule base on hydroxamic acid.

MMP inhibitors are well known to the art. For instance the inhibitors disclosed in WO 90/05716, WO 90/05719, WO 92/13831, EP-A-126,974, EP-A-159,396, U.S. Pat. Nos. 4,599,361 and 4,743,587 may all be used according to the present invention and the inhibitors disclosed therein are incorporated herein by reference.

Calcium chelators (e.g. EDTA), steroids (such as dexamethasone) and retinoic acid and derivatives thereof may also be used to prevent or treat connective tissue softening by reducing MMP activity.

We have found that MMP mediated remodelling of collagen is particularly significant in connective tissue softening. It is therefore preferred that the MMP inhibitor is a collagenase inhibitor. For instance, inhibitors of MMP 1 and MMP 8 are particularly useful for preventing connective tissue softening.

The present invention represents a surprising development given the teaching of the WO 95/24921. WO 95/24921 relates to the use of MMP inhibitors for preventing the contraction of tissues (such as scar tissues). Tissue contraction tends to develop over a long period of time (as scar tissue develops) whereas tissue softening is a different process that develops during the first 7 days (and up to 14 days) post injury. Furthermore contraction of tissues tends to result in tissues becoming harder and denser (as is observed when the fibrous tissue of a scar contracts). This would suggest WO 95/24921 teaches that MMP inhibitors may actually be used to "soften" dense scars. It is therefore surprising that, according to the present invention, MM? inhibitors may actually be used to prevent softening of connective tissues.

The medicaments of the invention may take a number of different forms depending, in particular on the manner in which the composition is to be used. Thus, for example, the medicament may be in the form of a powder, tablet, capsule liquid, ointment, cream, gel, hydrogel, aerosol, spray, micelle, liposome or any other suitable form that may be administered to a person or animal.

Medicaments will usually comprise at least an MMP inhibitor and a pharmaceutically acceptable vehicle. It will be appreciated that the vehicle should be one which is well tolerated by the subject to whom it is given and enables delivery of the MMP inhibitor to the target connective tissue. The vehicle is ideally biocompatible, biodegradable, bioresorbable and non-inflammatory.

The medicament may be used in a number of ways. For instance, a preferred means of administration of a MMP inhibitor for the prevention or reduction of connective tissue softening is by topical application. In this case liposomes, micelles, creams ointments gels and liquids may be used. A medicament according to the invention (in the form of an ointment or cream for example) may be applied to a tendon through an open wound (which may be an accidental injury or arise from elective surgery). Alternatively a MMP inhibitor may be incorporated in a micelle or liposome and delivered as a spray or aerosol to the target tissue. Softening of connective tissues occurs during the first few days after injury (usually up to 7 days but maybe up to 14 days) it is therefore preferred that a subject in need of treatment receives an MMP inhibitor during this time. Although it will be appreciated that different time courses of treatment may be required (e.g. for longer periods than 14 days or use as a prophylactic, e.g. prior to surgery, as stated above). In the case of repetitive strain injuries, involving chronic tissue softening, an MMP inhibitor should be administered until the softening has been reduced or eliminated to a clinician's satisfaction.

When a tendon or ligament needs to be sutured together following an injury it benefits the subject to be given MMP inhibitors pre-operatively (ideally as soon as possible after injury or in the case of elective surgery prior to and at the time of tendon/ligament incision) and for at least 7 days post-operatively (although up to 14 days or more may be required). Alternatively a clinician may choose to administer an MMP inhibitor until, or even beyond when, the sutures are removed or are resorbed.

When the connective tissue is accessible the MMP inhibitor is preferably administered topically. Alternatively a preferred treatment regime is injection of a liquid medicament to the injured site (for example an injection directly into the knee of a subject with injuries to the knee ligaments, tendons or cartilage). Such injections may need to be repeated several times and therefore an alternative, preferred regime is the utilisation of a device or carrier which will slowly release the MMP inhibitor over a desired period of time.

Systemic administration may be required. In this case the MMP inhibitor may be contained within a composition which may for example be ingested in tablet, capsule or liquid form or even be a liquid for injection into the blood stream or muscle. Systemic administration is particularly suitable for deep or major injuries.

Peptide MMP inhibitors (for instance peptide false substrates) may be used according to the present invention. When this is the case such peptide inhibitors may be provided by gene therapy. Such gene therapy is highly suitable for achieving sustained levels of active MMP inhibitor over a longer period of time than is possible for most conventional therapeutic regimes. Peptides may be continuously expressed from cells at an injury site which have been transformed with a DNA molecule coding for the peptide MMP inhibitor. Therefore, even if the peptide has a very short half-life life in vivo, therapeutically effective amounts of the inhibitor may be continuously expressed from the treated tissue. The DNA molecule provided by gene therapy for the treatment of connective tissue softening should be capable of being expressed (when administered to a subject) to produce a protein or peptide which may directly or indirectly have activity for treating connective tissue softening. By "directly" we mean that the product of gene expression per se has the required MMP inhibitor activity. By "indirectly" we mean that the product of gene expression undergoes or mediates (e.g. as an enzyme) at least one further reaction to provide an active MMP inhibitor (which may or may not be a peptide).

DNA molecules coding for peptide MMP inhibitors may be contained within a suitable vector to form a recombinant vector. The vector may for example be a plasmid, cosmid or phage. Such recombinant vectors are highly useful for transforming cells with the DNA molecule in gene therapy techniques. Furthermore, such recombinant vectors are useful for industrial production of MMP inhibitors. This industrial production may be by biotechnological means and utilise transformed cells in fermentors to produce the inhibitor. Alternatively the DNA molecules could be used to genetically engineer an organism to form a transgenic organism (ideally to form a transgenic placental mammal) which will express the MMP inhibitor and from which the expressed inhibitor may be harvested.

The MMP inhibitors discussed above are highly suitable for treating injured tissues, however, it will also be appreciated that the inhibitors may be used according to the present invention in a prophylactic manner. For instance, prior to elective surgery which involves severing a tendon or ligament, MMP inhibitors may be applied to the intact tendon or ligament in order that the tendon or ligament may subsequently heal with reduced or without softening occurring It will be appreciated that the amount of MMP inhibitor to be incorporated in medicaments in accordance with the invention depends on a number of factors. These include:

A) The efficacy of the inhibitor to be used.

B) The extent of the connective tissue injury to be treated.

C) The route of administration (possibly dictated by the location in the body of the injured tissue).

D) The half life of the inhibitor in the subject to which it is administered.

Purely by way of example a cream, ointment or gel containing a concentration of between 4 ng/ml–40 mg/ml of Galardin is suitable for topical application to an injured tendon. It is preferred that such a cream, ointment or gel contains a concentration of between 0.4 µg/ml–400 µg/ml.

The amount of such a cream, ointment or gel required will depend upon the specific condition to be treated. For instance, a small tear in a tendon of the finger may only require treatment with a few mls of the medicament, whereas a person suffering extensive injuries to the legs may require 100 mls or more of a cream, ointment or gel.

What is claimed is:

1. A method of preventing or treating a softening of connective tissue selected from the group consisting of a tendon, ligament or cartilage due to injury comprising administering to a subject in need of such treatment a therapeutically effective amount of a matrix metalloproteinase inhibitor.

2. The method according to claim 1, wherein the inhibitor is a collagenase inhibitor.

3. The method according to claim 1, wherein the inhibitor is a Tissue Inhibitor of Metalloproteinases (TIMP).

4. The method according to claim 1, wherein the inhibitor is an inhibitor of MMP1 or MMP8.

5. The method according to claim 1, wherein the inhibitor is BB-94.

6. The method according to claim 1, wherein the inhibitor is GM6001.

7. The method according to claim 1, wherein the inhibitor is a synthetic organic molecule based on hydroxamic acid.

8. The method according to claim 1, wherein the matrix metalloproteinase inhibitor is administered by topical application.

9. The method according to claim 1, wherein the matrix metalloproteinase inhibitor is administered by an injection.

10. The method according to claim 1, wherein the matrix metalloproteinase inhibitor is administered by a slow release device.

11. The method according to claim 1, wherein the matrix metalloproteinase inhibitor is administered in the first 14 days following injury.

* * * * *

UNITED STATES PATENT AND TRADEMARK OFFICE
CERTIFICATE OF CORRECTION

PATENT NO. : 6,455,569 B1 Page 1 of 1
DATED : September 24, 2002
INVENTOR(S) : Ferguson It is certified that error appears in the above-identified patent and that said Letters Patent is hereby corrected as shown below:

<u>Title page,</u>
Item "[73] Assignee: Renovo LTD, Manchester (DE)"

to read as

-- [73] Assignee: Renovo LTD, Manchester (UK) --.

Signed and Sealed this

Twentieth Day of May, 2003

JAMES E. ROGAN
*Director of the United States Patent and Trademark Office*